United States Patent [19]

Arndt et al.

[11] 4,239,876

[45] Dec. 16, 1980

[54] METHOD OF MAKING POLYMERIZABLE LIQUID MIXTURES

[75] Inventors: Peter J. Arndt, Seeheim-Jugenheim; Joachim Lowitz, Alsbach; Franz Wenzel, Darmstadt, all of Fed. Rep. of Germany

[73] Assignee: Röhm GmbH, Darmstadt, Fed. Rep. of Germany

[21] Appl. No.: 86,953

[22] Filed: Oct. 22, 1979

[30] Foreign Application Priority Data

Nov. 9, 1978 [DE] Fed. Rep. of Germany ....... 2848627

[51] Int. Cl.³ .......................................... C07C 103/54
[52] U.S. Cl. .................................... 526/287; 526/312; 526/75; 526/292; 560/222; 252/188.3 R
[58] Field of Search ................ 526/292, 287; 560/222; 260/561 N; 252/188.3 R

[56] References Cited

U.S. PATENT DOCUMENTS

| | | | |
|---|---|---|---|
| 2,741,568 | 4/1956 | Hayek | 117/139.5 |
| 2,810,713 | 10/1957 | Melamed | 260/561 N |
| 3,652,671 | 3/1972 | Barron | 260/561 N |
| 3,948,979 | 4/1976 | Patterson | 560/222 |
| 3,962,332 | 6/1976 | Trapasso | 260/560 N |
| 4,111,922 | 9/1978 | Beede et al. | 526/287 |
| 4,169,208 | 9/1979 | Kametani et al. | 560/222 |
| 4,180,643 | 12/1979 | Moss et al. | 260/561 N |

FOREIGN PATENT DOCUMENTS 2255391 5/1974 Fed. Rep. of Germany .
2537378 8/1974 Fed. Rep. of Germany .

*Primary Examiner*—Arthur P. Demers
*Attorney, Agent, or Firm*—Curtis, Morris & Safford

[57] ABSTRACT

What is disclosed is a method for the quaternization of tertiary aminoalkyl esters or tertiary aminoalkyl amides of acrylic acid or of methacrylic acid in admixture with from 30 to 80 percent, by weight of the mixture, of acrylamide employing an alkylating agent in the absence of water to form, in high yield and in short reaction time, a mixture containing the corresponding quaternization products in the form of a fluid mixture which can be used directly for the preparation of copolymers of acrylamide.

4 Claims, No Drawings

METHOD OF MAKING POLYMERIZABLE LIQUID MIXTURES

The present invention relates to a method for quaternizing an aminoalkyl ester or an aminoalkyl amide of acrylic acid or of methacrylic acid in the presence of acrylamide to give liquid mixtures which can be directly polymerized to form acrylamide copolymers.

The quaternizing products of tertiary aminoalkyl esters or aminoalkyl amides of acrylic acid or methacrylic acid are valuable starting materials for the preparation of water-soluble polymers, for example for the preparation of copolymers with acrylamide. The tertiary aminoalkyl esters and tertiary aminoalkyl amides of acrylic acid and methacrylic acid are liquids, whereas their quaternization products in pure form are solid salt-like compounds. On a technical scale, it is not possible to carry out the quaternization in a satisfactory manner with the addition of solvents or diluents since the reaction mixture gradually solidifes. Upon addition of organic solvents, such as acetone, for example, the quaternization mixture can be maintained in a stirrable condition until the conclusion of quaternization. However, the separation of the solvent represents an additional working step. If the quaternization is carried out in a highly-concentrated aqueous solution, the reaction product remains liquid and can be converted into a solid polymer gel. The presence of water in the quaternization and the subsequent polymerization, to be sure, brings about a partial hydrolysis of the ester groups or amide groups as well as, in some cases, that of the alkylating agent, so that the quaternization product is contaminated with the hydrolysis products of the alkylating agent and by free acrylic acid or methacrylic acid, or the subsequent polymer is contaminated by the presence of units of these acids.

The present invention has as its object the quaternization of tertiary aminoalkyl esters or tertiary aminoalkyl amides of acrylic acid or methacrylic acid in the absence of water, the maintenance of a stirrable system during the entire duration of the reaction, and the production of a reaction product that can be used directly for polymerization without an additional purification method or other working up.

The object has been achieved according to the present invention by carrying out the alkylation in the presence of acrylamide. The tertiary aminoalkyl ester or the tertiary aminoalkyl amide is subjected to the influence of the alkylating agent while in admixture with acrylamide. Acrylamide is a solid at room temperature and is only slightly soluble in the liquid aminoalkyl ester or aminoalkyl amide. During the course of the reaction, a liquid phase forms between the acrylamide and the quaternization product, in which liquid phase a complete reaction of the starting material can be achieved. The reaction takes place quickly and without side reactions; as the result of the absence of water, hydrolysis is excluded. The amount of the acrylamide in the mixture with the starting material to be alkylated is from 30 to 80 percent by weight.

The reaction product is a mixture of the salt-like quaternization product and acrylamide. It can be converted directly into the corresponding copolymer. Thus, the invention has its greatest significance as part of a method for preparing copolymers of this type.

The preferred starting materials are N,N-dialkylaminoalkyl esters and N,N-dialkylaminoalkyl amides of acrylic acid and methacrylic acid, but the group shall also include those compounds in which the alkyl groups present on the terminal nitrogen atom are joined together to form a piperidino, morpholino, or piperazino ring. Particularly preferred starting materials are N,N-dialkylaminoalkyl esters of acrylic acid and methacrylic acid in which the N-alkyl groups each contain 1 to 4 carbon atoms and the alkyl groups present between the amino nitrogen atom and the ester oxygen atom or amido nitrogen atom contain from 2 to 4 carbon atoms. The esters, in turn, are preferred over the amide. Exemplary of these esters are the dimethylaminoethyl ester, diethylaminoethyl ester, 2-dimethylaminopropyl ester, morpholinoethyl ester, N-butyl-N-methylaminoethyl ester, and the dibutylaminoethyl ester of acrylic acid or of methacrylic acid. As exemplary of starting materials having an amide structure, dimethylaminopropyl acrylamide and dimethylaminopropyl methacrylamide are particularly emphasized.

As alkylating agents, alkyl halides or dialkyl sulfates having 1 to 4 carbon atoms in the alkyl portion are preferred. Methyl chloride and dimethyl sulfate are particularly preferred. They are used in at least a stoichiometric amount. Methyl chloride has the particular advantage that any unreacted excess can be easily removed as a gas.

The reaction can be carried out continuously or discontinuously in simple stirred vessels which are suitably closed and have separate means for introducing acrylamide, the starting material to be quaternized, and the alkylating agent. As a rule, a polymerization inhibitor such as hydroquinone monomethyl ether is added during the quaternization to suppress any premature polymerization. Optionally, further free-radically polymerizable monomers, inert to the alkylating agent, can be added before, during, or after the quaternization reaction in order subsequently to convert the mixture into, for example, a terpolymer. Water-soluble monomers, such as methacrylamide, vinylpyrrolidone, and hydroxyalkyl esters of acrylic acid or of a methacrylic acid, and also water-insoluble monomers, in a limited scope, can be used for this purpose to the extent that they are miscible with the reaction product.

The reaction is carried out at temperatures above 30° C., preferably in the region from 35° C. to 100° C. In every case, the melting temperature of the mixture must be exceeded which, particularly when there is a low content of acrylamide, can make necessary the use of a reaction temperature of about 50° C. In order keep the danger of polymerization as minimal as possible, the temperature should not be chosen any higher than is required for the maintenance of homogeneity. During alkylation with gaseous alkylating agents, such as methyl chloride, the reaction is suitably carried out in a pressure vessel under 1 to 5 atmospheres. As a rule, after a period of reaction of from 15 to 60 minutes, a complete conversion is attained.

The liquid reaction product is preferably polymerized directly after preparation. For this purpose, a conventional free radical forming initiator, for example ammonium persulfate, hydrogen perioxide, or azo-bis-cyanovalerianic acid, or a redox system, can be added to the liquid reaction product and the latter can be polymerized in known fashion in a thin film, for example on a moving belt. The addition of small amounts of water before the beginning of polymerization promotes the homogeneity of the polymerizable final product. However, an aqueous solution of any desired concentration can be prepared and this can be polymerized according to known methods.

The resulting cationic copolymers of acrylamide are valuable auxiliary agents for the clarification of waste water and mud suspensions, retention agents in paper making, and thickening agents for aqueous liquids.

A better understanding of the present invention and of its many advantages will be had by referring to the following specific Examples, given by way of illustration.

EXAMPLE 1

3.5 kg of dimethylaminoethyl methacrylate and 10.85 kg of acrylamide are mixed with stirring in a 20 liter pressure kettle of VA steel (stainless steel). Methyl chloride is introduced into the closed vessel, whereupon the temperature rises rapidly and is maintained at 45° C.–50° C. by exterior cooling. The partial pressure of methyl chloride is adjusted to 3–3.5 atmospheres. After 50 minutes, the quaternization is terminated with a conversion above 99 percent. The product is liquid and contains small amounts of crystalline fractions which dissolve after the addition of some water.

EXAMPLE 2

The method according to Example 1 is repeated with a mixture of 8.2 kg of dimethylaminoethyl methacrylate and 7.2 kg of acrylamide. The partial pressure of methyl chloride is adjusted to 1.5–3.5 atmospheres and the temperature is maintained at 50° C. by cooling. After 60 minutes, a conversion of 99.5 percent is attained. The product is liquid and clear at 50° C.

EXAMPLE 3

2.75 kg of dimethylaminoethyl acrylate and 8.6 kg of acrylamide are mixed and quaternized at 50° C. with methyl chloride as described in Example 1. After 60 minutes, the quaternization product is obtained in 99.5 percent yield as a clear melt.

EXAMPLE 4

3.4 kg of dimethylaminopropyl methacrylamide and 4.4 kg of acrylamide are, as described in Example 1, mixed and quaternized at 50° C. with methyl chloride under a partial pressure of 1–2 atmospheres. After 90 minutes, the quaternization product is obtained in 99 percent yield at 50° C. as a viscous clear melt.

EXAMPLE 5

2.0 kg of diethylaminoethyl acrylate and 2.6 kg of acrylamide are mixed, as in Example 1, and quaternized at 60° C. with methyl chloride over three hours with a conversion of 97 percent. At 50° C., a clear melt is obtained.

EXAMPLE 6

4.6 kg of diethylaminoethyl acrylate and 7.8 kg of acrylamide are mixed in a closed coolable 20 liter VA-steel vessel and 3.4 kg of dimethyl sulfate is slowly added while the reaction temperature is not permitted to rise above 25° C. After 60 minutes, the quaternization is over. The melt, warmed to 50° C., and having a pH value of 8.0, is of low viscosity and clear and can be used for polymerization.

What is claimed is:

1. A method for making a liquid, directly-polymerizable mixture of acrylamide and a quaternization-product of a tertiary aminoalkyl ester or tertiary aminoalkyl amide of acrylic acid or of methacrylic acid which method comprises reacting said ester or amide with an alkylating agent in the absence of water while said ester or amide is in admixture with acrylamide such that the acrylamide is from 30 to 80 percent by weight of the mixture.

2. A method as in claim 1 wherein said ester or amide is an N,N-dialkylaminoalkyl ester or an N,N-dialkylaminoalkyl amide of acrylic acid or of methacrylic acid.

3. A method as in claim 2 wherein said N,N-dialkylaminoalkyl ester or N,N-dialkylaminoalkyl amide has from 1 to 4 carbon atoms in each N-alkyl group and from 2 to 4 carbon atoms in the alkyl-ester or alkyl-amido group.

4. A method as in claim 1 wherein said alkylating agent is an alkyl chloride or a dialkyl sulfate, each agent having 1 to 4 carbon atoms in the alkyl group or groups thereof.

* * * * *